US008691959B2

(12) United States Patent
Gerloni

(10) Patent No.: US 8,691,959 B2
(45) Date of Patent: Apr. 8, 2014

(54) PLASMIDS WITH IMMUNOLOGICAL ACTION

(75) Inventor: Mara Gerloni, San Diego, CA (US)

(73) Assignee: Cosmo Bio-Technologies SRL, Lainate (MI) (IT)

( * ) Notice: Subject to any disclaimer, the term of this patent is extended or adjusted under 35 U.S.C. 154(b) by 149 days.

(21) Appl. No.: 13/116,686

(22) Filed: May 26, 2011

(65) Prior Publication Data

US 2012/0076807 A1 Mar. 29, 2012

Related U.S. Application Data

(63) Continuation-in-part of application No. 12/377,114, filed as application No. PCT/EP2007/057224 on Jul. 13, 2007, now abandoned.

(30) Foreign Application Priority Data

Aug. 10, 2006 (EP) ..................................... 06118717

(51) Int. Cl.
*C07H 21/02* (2006.01)
*C07H 21/04* (2006.01)

(52) U.S. Cl.
USPC ....................................................... 536/23.1

(58) Field of Classification Search
None
See application file for complete search history.

(56) References Cited

U.S. PATENT DOCUMENTS 5,583,202 A 12/1996 Zanetti
7,425,606 B2 9/2008 Kosmatopoulos et al.

FOREIGN PATENT DOCUMENTS

| JP | 05-199865 | 10/1993 |
| WO | WO 90/09804 | 9/1990 |
| WO | WO 97/30721 | 8/1997 |
| WO | WO 00/02581 | 1/2000 |
| WO | WO 00/61766 | 10/2000 |
| WO | WO 00/64488 | 11/2000 |
| WO | WO 02/088306 | 11/2002 |
| WO | WO 2005/021595 | 3/2005 |
| WO | WO2005123762 | 12/2005 |

OTHER PUBLICATIONS

Attwood Science 2000; 290:471-473.*
Carol French and John M. Ward "Imrpoved Production and Stability of E. coli Recombinants Expressing Transketolase for Large Scale Biotransformation" Biotechnology Letters, vol. 17 No. 3 (Mar. 1995), pp. 247-252.
Attwood, "The Babel of Bioinformatics." *Science*, vol. 290, No. 5491, 2000, pp. 471-473.
Beyer et al., "Immunization with plasmid DNA expressing the caprine arthritis-encephalitis virus envelope gene: quantitative and qualitative aspects of antibody response to viral surface glycoprotein." *Vaccine*, vol. 19, 2001, pp. 1643-1651.
Billetta et al., "Major Histocompatibility Complex Class 1-Restricted Presentation of Influenza Virus Nucleoprotein Peptide by B Lymphoma Cells Harboring an Antibody Gene Antigenized with the Virus Peptide." *Eur. J. Immunol.*, vol. 25, No. 3, Mar. 1995, pp. 776-783.
Cardon et al., "Pervasive CpG suppression in animal mitochondrial genomes." *Proc. Natl. Acad. Sci.* USA, vol. 91, 1994, pp. 3799-3803.
Chen et al., "Cytotoxic T-cells Specific for Natural IgE Peptides Downregulate IgE Production." *Cellular Immunology*, vol. 233, Jan. 2005, pp. 11-22.
Gerloni et al., "Immunity to *Plasmodium Falciparum* Malaria Sporozoites by Somatic Transgene Immunization." *Nature Biotechnology*, vol. 15, No. 9, Sep. 1997, pp. 876-881.
Gurunathan et al., "DNA vaccines: a key for inducing long-term cellular immunity." *Current Opinion in Immunology*, 2000, pp. 12:442-447.
Krieg et al., "CpG motifs in bacterial DNA trigger direct B-cell activation." *Nature*, vol. 374, 1995, pp. 546-549.
Le et al., "Safety, tolerability and humoral immune responses after intramuscular administration of a malaria DNA vaccine to healthy adult volunteers." *Vaccine*, vol. 18, 2000, pp. 1893-1901.
Minutes of Meeting, Sep. 19-20, 2002, Recombinant DNA Advisory Committee. *Human Gene Therapy*, vol. 14, pp. 313-327.
Pulendran et al., "Translating Innate Immunity into Immunological Memory: Implications for Vaccine Development." *Cell*, vol. 124, 2006, pp. 849-863.
Roman et al., "Immunostimulatory DNA sequences function as T helper-1-promoting adjuvants." *Nature Medicine*, vol. 3(8), 1997, pp. 849-854.
Roy et al., "Induction of antigen-specific CD8+ T cells, T helper cells, and protective levels of antibody in humans by particle-mediated administration of a hepatitis B virus DNA vaccine." *Vaccine*, vol. 19, 2001, pp. 764-778.
Sato et al., "Immunostimulatory DNA Sequences Necessary for Effective Intradermal Gene Immunization." *Science*, vol. 273, 1996, pp. 352-354.
Sollazzo, "Molecular Characterization of the $V_H$ Region of Murine Autoantibodies from Neonatal and Adult BALB/c Mice." *Eur. J. Immunol.*, vol. 19, No. 3, 1989, pp. 453-457.
Takagi et al. "Method of Experiment on Gene Manipulation." *Kodansha Ltd*. Jul. 1, 1981. pp. 79—Englisth Translation Provided.
Timmerman et al., "Immunogenicity of a Plasmid DNA Vaccine Encoding Chimeric Idiotype in Patients with B-Cell Lymphoma." *Cancer Research*, vol. 62, 2002, pp. 5845-5852.
Wang et al., "Induction of CD4+ T cell-dependent CD8+ type 1 responses in humans by a malaria DNA vaccine." *Proc. Natl. Acad. Sci.*, vol. 98(19), 2001, pp. 10817-10822.
Xiong et al., "Engineering Vaccines with Heterologous Band T Cell Epitopes Using Immunoglobulin Genes." *Nature Biotechnology*, vol. 15, No. 9, Sep. 1997, pp. 882-886.

(Continued)

*Primary Examiner* — Michail Belyavskyi
(74) *Attorney, Agent, or Firm* — Merchant & Gould P.C.

(57) ABSTRACT

Recombinant plasmids usable for the transfection of eukaryotic and prokaryotic cells are described; such plasmids have a length comprised between 7 and 12 kbases and comprise a sequence encoding the heavy chain of an immunoglobulin; in particular, they may be used:
  in a process of transfection of prokaryotic or eukaryotic cells (ex vivo) which can be inoculated into higher organisms in order to induce a prophylactic or therapeutic immune response;
  in a protocol of direct inoculation (in vivo) in higher organisms in genic immunization methodologies with the aim of evoking prophylactic or therapeutic immune responses.

1 Claim, 5 Drawing Sheets

(56) References Cited

OTHER PUBLICATIONS

Xiong et al., "In Vivo Role of B Lymphocytes in Somatic Transgene Immunization." *Proceedings of the Natl. Acad. Of Sciences of the U.S.*, vol. 94, Jun. 1997, pp. 6352-6357.

Yang et al., "A DNA vaccine induces SARS coronavirus neutralization and protective immunity in mice." *Nature*, vol. 428(1), 2004, pp. 561-564.

* cited by examiner

Figure 1. Map of plasmid 1
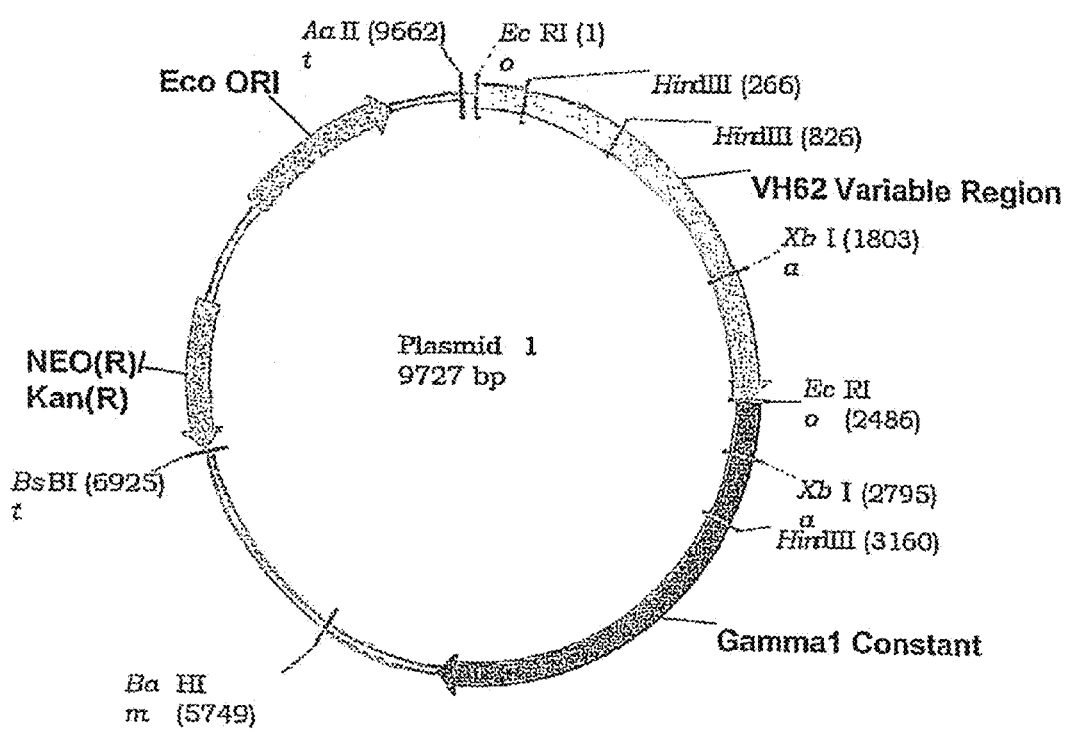
| | |
|---|---|
| 1-2483bp | Segment encoding the variable region Vh62 |
| 2484-5077 bp | Segment encoding the constant region γ1 |
| 6943-7737bp | Segment encoding the gene for resistance to neomycin |
| 9324-9267bp | E. coli origin of replication |

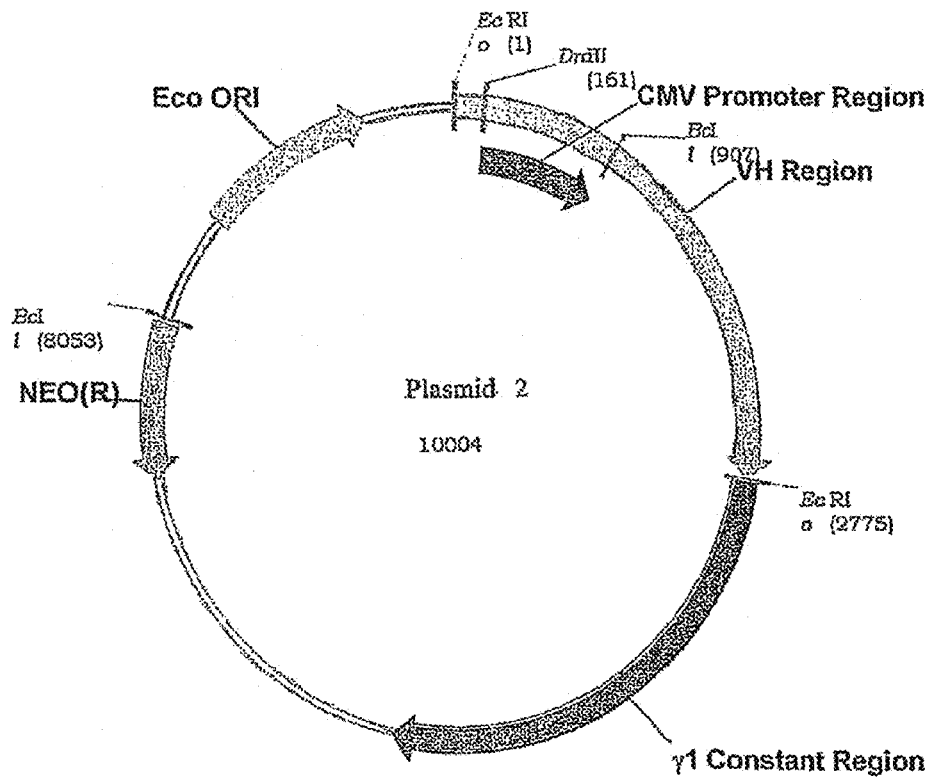
Figure 2. Map of plasmid 2
| | |
|---|---|
| 1 to 2775 | Segment encoding the variable region Vh62 |
| 161 to 907 | Viral promoter CMV |
| 2776 to 5366bp | Segment encoding the constant region γ1 |
| 7232 to 8026bp | Segment encoding the gene for resistance to neomycin |
| 8613bp to 9553bp | E. coli origin of replication |

Figure 3. Diagrammatic representation of a model of insertion of epitopes into the CDRs of the plasmid
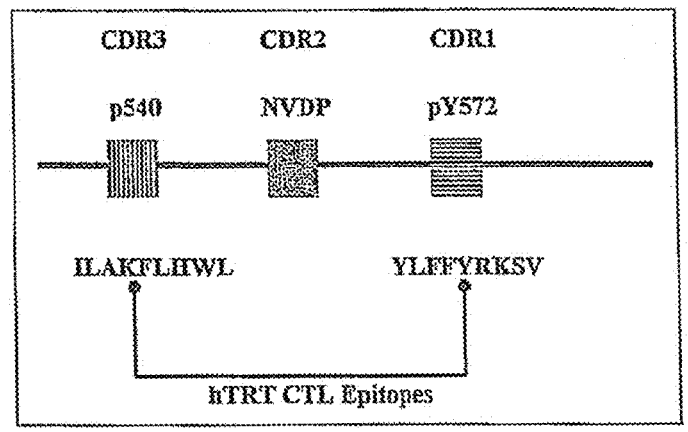
Figure 4. Hypothethised structure of a protein with antigenic epitopes that is encoded by the plasmid described Figure 5. Restriction map of the plasmids
| Restriction enzyme | Originated fragments Plasmid 1 | Originated fragments Plasmid 2 |
|---|---|---|
| EcoRI | 2.5kb + 7.2kb | 2.6kb + 7.2kb |
| XbaI | 1kb + 8.7kb | 1kb + 8.8kb |
| BamHI | 9.7kb | 9.8kb |
| HindIII | 0.5kb + 2.4kb + 4.9kb + 1.9kb | 0.5kb + 2.3kb + 7.0kb + 1.9kb |
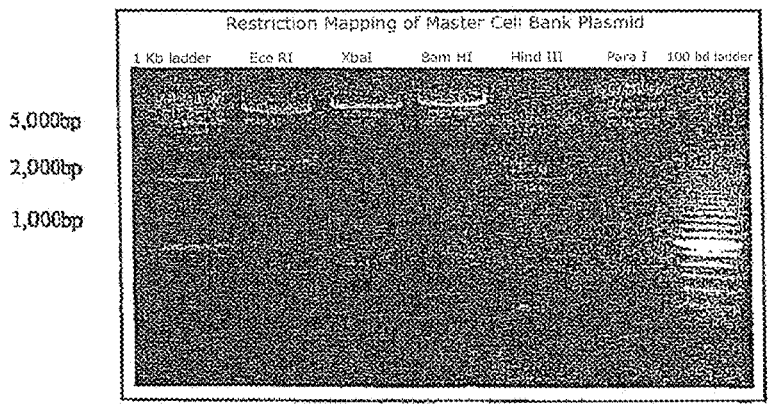

Figure 6. Amplification by means of PCR test of the plasmid from lymphocytes transfected ex vivo
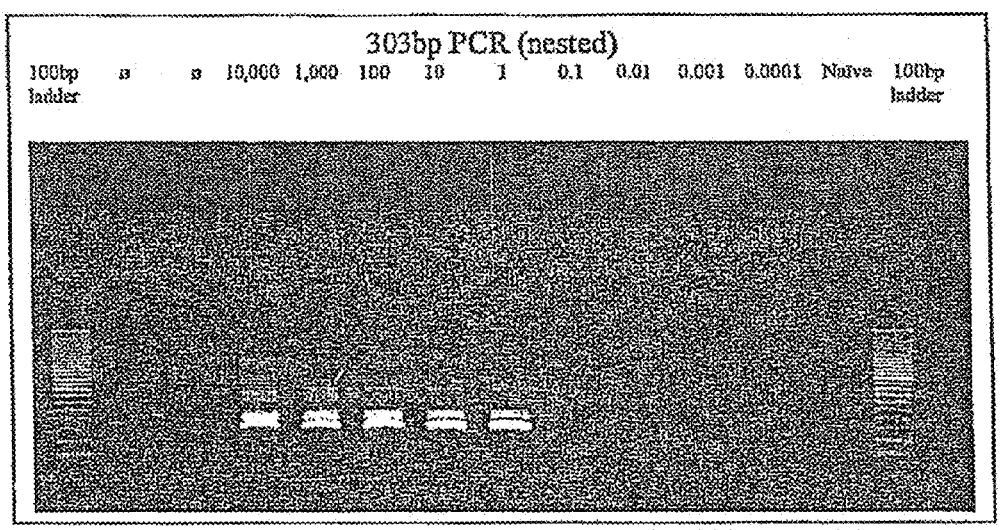

PLASMIDS WITH IMMUNOLOGICAL ACTION

CROSS-REFERENCE TO PRIOR APPLICATIONS

This is a Continuation-in-Part of U.S. Ser. No. 12/377,114, filed Feb. 10, 2010, which is a U.S. National Phase Application under 35 U.S.C. §371 of International Patent Application No. PCT/EP2007/057224 filed Jul. 13, 2007, which claims the benefit of European Patent Application No. 06118717.5, filed Aug. 10, 2006, and which applications are incorporated by reference herein. The International Application was published in English on Feb. 14, 2008 as WO 2008/017568 A1 under PCT Article 21(2). To the extent appropriate, a claim of priority is made to each of the above disclosed applications.

The object of the present invention is represented by a recombinant plasmid usable for the transfection of eukaryotic and prokaryotic cells, having a length comprised between 7 and 12 kbases and comprising a sequence encoding the heavy chain of the immunoglobulin. A further object of the invention is represented by the use of the aforesaid plasmid for the preparation of a pharmaceutical formulation, or of a vaccine or a therapeutic treatment, for inducing an immune response in a human or animal organism.

In particular, described and claimed is a sequence of bases that are used for the construction of plasmids which may be used:

- in a process of transfection of prokaryotic or eukaryotic cells (ex vivo) which can be inoculated into higher organisms in order to induce a prophylactic or therapeutic immune response (in particular by means of the plasmid 1 having the sequence SEQ ID NO: 1);
- in a protocol of direct inoculation (in vivo) into higher organisms in genic immunization methodologies in order to evoke prophylactic or therapeutic immune responses (in particular by means of the plasmid 2 having the sequence SEQ ID NO: 2).

A description is also given of a profile of pathologies which may be treated with the plasmids described.

STATE OF THE ART

DNA of plasmidic origin may be used for the transfection of prokaryotic and eukaryotic cells through known methods. The plasmids constructed for this purpose are generally constituted by a skeleton which has inserted units of genetic material encoding a certain protein which may or may not be provided with its own biological activity.

The plasmids may be of commercial origin, into which a part bearing the specificity is introduced into a structural construct that is already known and used, or generated autonomously, that is, by assembling fragments of selected genetic material on the basis of a certain profile to be reconstructed at the organism for which the plasmid is destined.

The synthesis of a plasmid is an operation of fundamental importance for the purpose of obtaining the desired cellular properties. The plasmids determine the efficiency of the transfection and of the synthesis of the transgenic protein, and also the safety of the transfection, and therefore in the final analysis the resultant efficacy of the proteic expression of the transfected cell.

A plasmid is a vector of genetic data which influence the cellular cycle of the host cell and, consequently, the life cycle of the organism which hosts these transfected cells: the more data introduced into the plasmid, the more risks are run in the course of the transfection.

A plasmid is characterized by the specificity of the data contained: the less complex it is, the easier the synthesis thereof and the safer the use thereof.

A plasmid exercises the capacity of transfecting a cellular population more or less spontaneously depending on the type of cell and the experimental conditions of contact/incubation in which transfection is carried out. The more selective a plasmid is for a specific cellular population, the more it is usable in conditions of safety.

The conditions in which transfection is carried out are decisive for the success thereof: the homogeneity and the concentration of the cells to be transfected, the incubation time and conditions, the possibility of monitoring the phenomenon with specific and selective methods constitute an extremely important corollary for the success of the operation.

In the specific case in which a plasmid is used for transfecting cells to be injected in vivo in patients, such cells are to be handled with extreme caution inasmuch as they must be re-inserted into the patient, and risky and fatal collateral phenomena cannot be risked: the less handling is necessary, the greater the safety of the method and the more reproducible the result.

From the above it inevitably follows that the use of a plasmid of reduced dimensions, especially if combined with a method with limited handling, is a condition to be preferred in transfection used for prophylactic and therapeutic purposes.

The use of a plasmid encoding immunogenic epitopes in an autologous transfection method is one of the systems that can be used for inducing a specific immune response in some pathologies characterized by the appearance of infecting agents, or by spontaneous or induced cellular mutation (carcinogenesis), with modification of the apoptotic course of a selected cell or cellular line.

WO 90/09804 describes immunoglobulins genetically engineered for expressing a predefined peptide epitope in the variable region or in the bond domain of the immunoglobulin.

WO 00/61766 describes tumoral antigens derived from telomerasis that can be used for generating a response mediated by T-cells against telomerasis and consequently against the tumour itself.

WO 00/64488 describes a plasmid encoding chimeric heavy chain of an immunoglobulin, the $pN\gamma_1 V_H 62$ plasmid, which is obtained by subcloning the murine $V_H 62$ gene into the $pN\gamma_1$ plasmid, containing a sequence encoding a human $\gamma_1$ costant region. This plasmid can be modified by introduction of heterologous epitopes in any of the complementarity determining regions of the variable region. Therefore, its use in a method for inducing an immunoresponse is disclosed.

However, the $pN\gamma_1 V_H 62$ plasmid contains portions that will be harmful if this plasmid would be injected into humans. Furthermore, the dimensions of this plasmid are such that a very low transfection yield is obtained.

BRIEF DESCRIPTION OF THE DRAWINGS

FIG. 1: Map of Plasmid 1 where I-2483 bp is the segment encoding the variable region Vh62, 2484-5077 bp is the segment encoding the constant region γ1, 6943-7737 bp is the segment encoding the gene for resistance to neomycin, and 9324-9267 bp is the *E. coli* origin of replication.

FIG. 2: Map of Plasmid 2 where 1 to 2775 is the segment encoding the variable region vh62, 161 to 907 is the viral promoter CMV, 2776-5366 bp is the segment encoding the constant region γ1, 7232 to 8026 bp is the segment encoding the gene for resistance to neomycin and 8613 bp to 9553 bp is the *E. coli* origin of replication.

FIG. 3: Diagrammatic representation of a model of insertion of epitopes into the CDRs of the plasmid.

FIG. 4: Hypothesized structure of a protein with antigenic epitopes that is encoded by the plasmid described.

FIG. 5: Restriction map of the plasmids.

FIG. 6: Amplification by means of PCT test of the plasmid from lymphocytes transfected ex vivo.

DESCRIPTION OF THE INVENTION

The present inventors have now developed plasmids comprising a sequence encoding the heavy chain of immunoglobulin that do not present the drawbacks of the pNγ$_1$V$_H$62 plasmid when used for inducing an immunoresponse in vivo or ex vivo in a human or animal organism. In particular, the plasmids developed have a better safety profile and show an increase yield when transfected into cells.

These plasmids have a length comprised between 7 and 12 kbases, preferably between 8 and 12 kbases, more preferably between 9 and 11 kbases and, even more preferably, between 9 and 10 kbases and are able to express the heavy chain of immunoglobulin when they are transfected into lymphocytes.

According to a preferred embodiment, these plasmids express a chimeric heavy chain of immunoglobulin, preferably comprising a murine variable region and a human constant region, preferably Igγ1. The murine variable region is preferably the V$_H$ region from hybridoma 62 derived from splenocytes of an adult hyperimmunised mouse (Zanetti et al. J. Immunol., 1983, 131:2452), hereinafter referred to as V$_H$62 region. The V$_H$62 hybridoma 62 secretes a monoclonal antibody with anti-tyroglobulin activity The Igγ1 region gene is preferably cloned from the vector pNγ1.

The plasmids may further contain a promoter specific for lymphocytic cells, preferably of around 50 bp, or of viral origin, preferably the CMV promoter.

The plasmids of the invention preferably also comprise the polyadenylation sequence AATAAA.

It is preferred that the plasmids of the invention do not express resistance to betalactamic antibiotics and in particular to ampicillin, and/or do not comprise a replication origin of SV40.

Accordingly, the plasmids preferably contain a replication origin of *Escherichia coli*, preferably PBR322. Furthermore, the plasmids preferably express resistance to neomycin.

Preferred plasmids of the invention are plasmids 1 and 2.

The plasmid 1 has a length of 9727 bp (SEQ ID NO: 1 and FIG. 1) and the plasmid 2 of 10004 bp (SEQ ID NO: 2 and FIG. 2). Both the plasmids described encode a chimeric heavy chain of immunoglobulin.

The sole structural difference between the two plasmids is determined by the specific promoter, which in the case of the plasmid 1 is a specific promoter for lymphocytic cells of 50 bp, and in the case of the plasmid 2 is a viral promoter with dimension of 742 bp.

The skeleton of the plasmids is represented by pSV2neo, a DNA of bacterial origin containing the gene for resistance to neomycin and the origin of replication PBR322.

The genetic sequence encoding the heavy immunoglobulinic chain is composed of:

a murine variable region (V$_H$62) of around 2.5 kb, originally cloned from a mouse hybridoma (hybridoma 62) secreting a monoclonal antibody with anti-tyroglobulin activity (Sollazzo, et. al., *Eur. J. Immunol.*, 1989);

a human Igγ1 constant region deriving from the pNγ1 vector (Hybritech Corporation, San Diego, Calif.).

The immunoglobulinic promoter of the plasmid 1 is an integral part of V$_H$62, while the viral promoter of the plasmid 2 was derived from the plasmid phMGFP (Promega, Wis., USA). The gene for resistance to neomycin also confers a resistance to kanamycin for selective growth in prokaryotic cells.

The polyadenylation sequence is in position 5178:5183 of the plasmid and follows the human constant region. The sequence is as follows: AATAAA. The origin of bacterial replication is of *Escherichia coli* and is situated in position 8324:9264.

The particular feature of the plasmids of the invention is that the regions determining the complementarity (CDR) of the encoded protein may be mutagenized for the purpose of introducing therein epitopes (from 5 to 25 amino acid residues) with antigenic properties (Gerloni et al Nature Biotechnology 1997). Such properties make it possible to use the plasmid in question for inducing a specific immune response either by means of a transfection ex vivo with the inoculum of cells transfected spontaneously or by means of direct inoculation in vivo (genic immunization).

Accordingly, an object of the present invention is the use of the plasmids of the invention for the preparation of a pharmaceutical formulation for DNA vaccination, in particular for inducing an immunoresponse in a human or animal organism. Furthermore, another object of the invention is a formulation containing at least one plasmid according to any one of the preceding claims together with pharmaceutically acceptable excipients and/or coadjuvants.

The formulation of the invention may be used for prophylactic or therapeutic purposes.

The formulation of the invention may be used in particular in a human or animal organism that is or was affected by:

tumours belonging to the family of carcinomas and/or adenomas and/or sarcomas and/or lipomas and/or solid and/or ascitic tumours, by prostate or pancreatic, renal or pulmonary carcinoma. Preferably, in this case said organism is or was affected by the presence of tumour cells having on the surface at least one antigenic epitope, the encoding sequence of which is contained in the plasmid.

bacterial, viral, fungal and/or parasitic infections.

A further object of the present invention is a method for inducing an immunoresponse in a human or animal organism. Said method comprised transfection of prokaryotic and/or eukaryotic cells ex vivo and the subsequent inoculation of said prokaryotic and/or eukaryotic cells into said human or animal organism. Preferably, said transfected cells belong to the family of limphocytes and are preferably taken from the peripheral vessels of said human or animal organism. Alternatively, said method comprises inoculation of the plasmid in vivo into said human or animal organism.

Inoculation of the plasmid or of the prokaryotic and/or eukaryotic cells into said human or animal organism is preferably carried out by means of injective or transmucosal administration.

The protein encoded by the plasmids of the invention, like all the immunoglobulins, possesses 3 CDRs, CDR1 with a restriction site usable for the insertion of peptide sequences AfiIII, CDR2 with a NcoI site and CDR3 with an Acc65I site.

It is therefore possible to insert into them various peptide sequences capable of evoking various immune responses both of the humoral type (mediated by B cells) and of the cellular mediated type (mediated by T-cells CD4 and CD8); for example, it is possible to insert at least a single sequence on each CDR, for a total of three sequences capable of evoking various immune responses; it is further possible to insert one or more sequences, optionally fused with one another, on each CDR.

An example of insertion of antigenic epitopes into the CDRs is shown in FIG. 3.

The antigenic epitopes preferred for the purposes of the present invention are:

tumoral antigens, such as for example that of telomerasis and, even more preferably, p540 (ILAKFLHWL; SEQ. ID NO: 3), p572 (RLFFYRKSV; SEQ. ID NO: 4), pY572 (YLFFYRKSV; SEQ. ID NO: 5) and p865 (RLVDDFLLV; SEQ. ID NO: 6);

antigens deriving from infective microorganisms, such as, for example, that of influenza and, preferably, the epitope pNP (ASNENMETM; SEQ. ID NO: 7).

The transgenic product encoded plasmids 1 and 2 is a protein with a molecular weight of around 156.000 daltons (FIG. 4). The heavy region encoded is chimeric in nature: part human (the constant region) and part murine (the variable region). Nevertheless, the murine part contains sequences 80% homologous with the human variable regions.

Important characteristics of the aforesaid plasmids are the absence of the gene for resistance to ampicillin and the presence of the gene for resistance to kanamycin which provides for the safe use thereof in subjects with potential allergies to the betalactamic antibiotics. Another advantageous factor is that kanamycin is an antibiotic stable at 37° C. (conditions of culture of the plasmid) for 24-48 hours, while ampicillin is stable only for 3-4 hours, consequently allowing a culture yield of the plasmid which is greater (less expensive production) and more stable.

The aforesaid plasmids are also devoid of "useless" sequences (for example the sequence SV40 or pieces of genomic material) which would represent greater risks of homology with the genome of the host cell and therefore greater risks of integration in the cell itself.

Analysis of the Restriction Map of the Plasmids

The restriction map obtained by digestion with restriction enzymes is the first criterion to be considered in order to define the identity of a plasmid. In particular, the map shown in FIG. 5 identifies in an exclusive manner the plasmids 1 and 2. There is also shown in succession an image of the fragments of the plasmid 1 after digestion, run on agarose gel in parallel with a standard of known dimension (1 Kb ladder) in order to determine the exact dimension thereof. The sequence of the plasmid 1 is shown in SEQ ID NO: 1, while the sequence of the plasmid 2 is shown in SEQ ID NO: 2.

Biological Characterization of the Plasmids

It has already been indicated previously that a plasmid encoding immunogenic epitopes in a method of transfection is one of the systems that can be used for inducing a specific immune response in some pathologies characterized by the appearance of infecting agents, or by spontaneous or induced cellular mutation (carcinogenesis), with modification of the apoptic course of a selected cell or cellular line.

A further use for such a plasmid is the direct injection in vivo into immuno-competent organisms in order to induce an immune response against proteins of a foreign nature and pathogenic microorganisms (Tang et al., *Nature* 1992, Ulmer et al., *Science* 1993, Gerloni et al., *Nature Biotechnology* 1997). In this field with the inoculation of functional genes the induction of humoral responses (mediated by antibodies) and cellular mediated responses (mediated by T-lymphocytes of type CD4 and CD8) effective in the treatment or prevention of pathologies of infective and cancerous origin was demonstrated.

Consequently, the concept of genic immunization is now adopted by vaccinologists all over the world, who use plasmids encoding antigens deriving from bacteria, viruses and parasites and also from various types of tumour in order to evoke specific and protective immune responses. Clinical trials are currently under way for the therapy or prophylaxis of HIV, herpes, influenza, avian influenza, SARS, hepatitis B and C and carcinomas of various kinds.

The essential components of a plasmid to be used in vivo are the gene encoding the antigen (or pieces thereof) of interest, a promoter sequence (normally derived from cytomegalovirus, CMV) which guides the transcription of the antigen, a region of polyadenylation which ensures the translation thereof.

Furthermore, together with the origin of replication for the amplification of the plasmid in bacterial cells there is also a gene which encodes antibiotic resistance in order to ensure the selection of the bacterial population and to eliminate contamination during culture.

Another intrinsic property of the DNA vaccines is that plasmids of bacterial origin contain sequences of non-methylated cytosine together with residues of guanosine (CpG). These CpG units have the capacity of increasing the immunogenic capacity of the plasmids themselves and therefore function as adjuvants.

The direct inoculation of nucleic acids into somatic cells appears to mimic the immunity induced by natural infections and offers various advantages, including the possibility of producing and testing such plasmids in an inexpensive, easy and rapid manner. Moreover, the plasmids are much more stable than conventional vaccines and may be preserved as lyophilisates.

The plasmid is usually inoculated in vivo by the intramuscular or intradermal route, although other routes such as the oral, vaginal, endovenous, intraperitoneal and subcutaneous routes are applicable. The plasmids are administered in a variety of diluents which include distilled water, saline or sugar solutions, physiological buffers, isotonicising compounds, preservative or cryoprotective substances in case the processes of lyophilisation are necessary.

The dose of plasmid used in the immunization protocols varies from case to case but, as a rule, amounts of from 25 to 200 µg per dose are used with 3 doses/injections at intervals of three weeks.

A further object of the present invention is therefore constituted by two recombinant plasmids characterized by a sequence corresponding to SEQ ID NO: 1 and SEQ ID NO: 2, respectively or a sequence at least 90% homologous, preferably 95% homologous to SEQ ID NO. 1 and SEQ ID NO: 2. These plasmids have dimensions that are reduced but suitable for the purpose and a transfection method that is suitable, reproducible, safe and effective.

The use of such plasmids has specific characteristics:

optimum yield in the production process, inasmuch as a plasmid of measured content is simpler to produce and gives rise to better production yields if reduced in amplitude;

optimum stability of the cellular culture, since the plasmids contains the gene for resistance to antibiotic kanamycin stable at 37° C. for 24-48 hours (as opposed to ampicillin stable only for 4-6 hours at the same temperature) the stability of the bacterial culture is consequently significantly increased, with undoubted advantages in terms of yield;

high efficiency of spontaneous transfection (capacity of penetration into the cell) because of contained molecular dimensions and lesser steric bulk, a not negligible detail in the case of protocols in which the use of spontaneous transfection is envisaged;

the absence of the possibility of anaphylactic reactions that can be induced in the subjects treated, if predisposed to an allergic reaction to ampicillin, inasmuch as the plasmid, not possessing the gene for resistance to ampicillin, is not grown in the presence of that antibiotic;

low, if not zero, possibility of integration in the genome of the host cell inasmuch as the minimum quantity of plasmid used for transfection renders practically negligible the risk of integration (consequently reduced possibility of induction of oncogenic mutations in the host cell);

low, if not zero, possibility of direct integration in the genome of the host cell inasmuch as the plasmid does not possess extraneous sequences (such as SV40) which could have homologies with the genome of the cell itself and represent greater risks of integration;

high flexibility of use of the plasmid also for direction injection in vivo in genic immunization protocols. In fact, by substituting in the nucleotidic sequence the specific promoter for B cells with a viral promoter (CMV) with wider expression, the use of the plasmid is extended by simple transfection ex vivo to the use of direct inoculation in higher organisms.

A further object of the present invention is constituted by the use of a method of transfection ex vivo without the use of any physical or chemical means which might facilitate the process. Such a method does not induce disturbances in the functionality of the transfected cells and does not induce genetic transformation thereof. The method is characterized by separation of the specific cellular material to be transfected from the remainder of the corpuscular and fluid part of the peripheral blood, obtainable with processes with less handling than the normal centrifuging methods: the use of apheresis makes it possible to separate a large number of lymphocytic cells on which to carry out transfection in a manner which is painless for the patient and very much more useful for experimental purposes. In fact:

it does not disturb the functionality of the cells with gravitational or mechanical shocks;

it allows the harvesting of a large number of cells, to be used for the process and to keep stored as reference for the subsequent phase of therapeutic monitoring;

it does not impoverish the functional and structural resources of the patient or his coagulative or reparative processes;

it does not add any risk of contamination of the biological material and/or of the patient.

An object of the present invention is constituted by the use of a plasmid as described for effecting the transfection ex vivo of selected cells by means of a spontaneous process with the adoption of the following modalities:

1. transfer of the peripheral blood originating from a patient into an instrument capable of directly separating the family of lymphocytes from the rest of the corpuscular fraction and from the serum (apheresis process);
2. isolation of a quantity of lymphocytic cells suitable for the application of the treatment described hereinafter; then transfer of the isolated lymphocytes and washing with PBS (without $Ca^{++}$ and $Mg^{++}$) and further centrifuging;
3. dilution 1:1 with tryptan blue and counting of the lymphocytes via haemocytometer and microscope in order to verify that they have preserved at least 90% of vitality;
4. re-suspension of the lymphocytes at a concentration of around $20 \times 10^6$ cells/ml in PBS (without $Ca^{++}$ and $Mg^{++}$) and re-division of an aliquot into plates with U-shaped wells, where 25 μg of a plasmid having the sequence shown in SEQ ID NO: 1 are added;
5. incubation of the plates with the transfection wells in an incubator for 30-90 minutes at 37° C. and 5% of $CO_2$;
6. transfer of a suitable aliquot of cells treated with plasmid into a suitable culture medium and leaving to incubate for one night;
7. verifying that the cellular vitality is maintained above a threshold judged to be appropriate (typically 70%) and calculating the dose to be transferred to the patient;
8. transfer into a phleboclysis bag of a suitable volume of transfected cells containing the dose to be re-administered to the patient (typically variable from a few thousands to a few tens of millions of cells);
9. within the scope of the treatment intended to arouse an immune response against the cells which express at the surface the proteins of which the epitopes are contained in the plasmid, inoculation into the patient of the blood contained in the bag, transgenized by means of the use of the plasmid having the sequence shown in SEQ ID NO: 1.

As an alternative to the method described above, the isolation of the lymphocytes to be transfected may also be carried out by a classic method based on centrifuging; in that case the treatment of apheresis described above in item 1 and item 2 may be substituted by the following:

1. transfer of the peripheral blood originating from a patient into test tubes, addition of buffer with Ficoll and centrifuging until the lymphocytes stratify into an unmistakable band;
2. transfer of the isolated lymphocytes and washing with PBS (without $Ca^{++}$ and $Mg^{++}$) and further centrifuging.

The use of the plasmid of reduced dimensions and a selected population of cells as described above makes it possible to obtain advantages from the process, such as a reduced time for handling of the blood and of its lymphocytic fraction, a reduced incubation time, a substantially reproducible process yield, the possibility of applying a high degree of automation to the various steps of the process and the possibility of performing the transfection process directly inside an isolated device which does not require the adoption of sterile conditions of the working ambience outside the device itself, which are required by the handling of biological fluids intended for human administration.

A object of the present invention is constituted by the use of a plasmid of contained dimension and characterized by the sequence described, with a method of isolation of the material to be transfected with reduced handling, with transfection conditions described for inducing immune responses in the treated patients against the agent responsible for the infection or the mutation, of which the specific imprint at the sequential and conformational level is contained in the genetic material represented in the plasmid.

A further object of the present invention is constituted by the use of a device in which to carry out the incubation of the plasmid with the cells, characterized by the presence of a space in which to accommodate the desired volume of cells, a port through which to insert a needle in order to deposit a solution of the plasmid and an optional other port through which to effect the sampling of the transfected cells.

In a typical application of the present invention, the plasmid with the sequence shown in SEQ ID NO: 1 is used on a population of lymphocytic cells separated from the blood by the method of apheresis; these transfected cells, after incubation under the normal conditions used for biological fluids, are injected back into a patient in order to induce an immune type of response.

In a further application of the present invention, the plasmid constructed as described is used under the conditions described for transfecting a population of lymphocytic cells harvested by means of apheresis or centrifuging from a patient affected by a tumour of the pancreas, or prostate, lung, kidney, or skin, or affected by some other type of adenomatous or carcinomatous or other tumoral form, either solid or acytic in form, in order to induce in the patient himself a selective immune response against only the cancerous cells, expressing superficially the proteic fraction contained in the plasmid and by these caused to express the lymphocytes, used as APC (cells presenting the antigen).

In a further application of the present invention, the plasmid shown in SEQ ID NO: 1 is modified by the substitution of the promoter for lymphocytic cells with a promoter of viral origin (CMV). Such substitution gives rise to a plasmid of slightly larger dimensions (300 bp), shown in SEQ ID NO: 2, and used for inducing an immune response in an organism by means of direct parenteral (intramuscular, intradermal, subcutaneous or endovenous) administration or transmucosal administration (via the nasal, oral, intestinal or vaginal mucosa).

The plasmids described were evaluated for:
1. the capacity for spontaneously transfecting human lymphocytes;
2. the capacity for inducing an immune response in laboratory mice when injected with transfected cells ex vivo;
3. the capacity for inducing an immune response in laboratory mice when injected directly with the plasmid 2 in a genic immunization protocol.

The following examples are intended purely as non-limiting illustrations of the invention.

The plasmid 1 was constructed according to the following protocol:
1. Modification of the plasmid PSV2 neo
   The plasmid PSV2 neo was digested with the restriction enzymes AhdI and XmnI in order to remove the segment for resistance to ampicillin ($amp^r$)
   PSV2 neo ($amp^r$ minus) was digested with BsmBI and HindIII in order to remove the origin of replication SV40 (SV40)
   PSV2 neo ($amp^{r\ and\ SV40}$ minus) was digested with AatII and BstBI. At the end of this process a fragment of 2737 pairs of bases containing the origin of replication of *E. Coli* and the gene for resistance to neomycin/kanamycin was obtained. This fragment was isolated from agarose gel, purified on a column and maintained at 4° C. until subsequent use.
2. Modification of the plasmid γ1Vh62
   The plasmid $\gamma 1V_H 62$ was digested with the restriction enzymes FseI and BamHI in order to remove the segment of 4787 pairs of bases encoding human genomic DNA
   The plasmid thus derived ($DNA^{genomic}$ minus) was circularised with the new dimension of 10721 pairs of bases. It was digested with AatII and BstBI and the fragment containing the variable and constant region was purified for the subsequent ligation reaction
3. Construction of the final plasmid 1
   The plasmid PSV2 neo ($amp^{r\ and\ SV40}$ minus) deriving from the passage 1 was digested with AatII and BstBI.
   The modified plasmid $\gamma 1V_H 62$ ($DNA^{genomic}$ minus) deriving from the passage 2 was digested with AatII and BstBI.
   The two modified plasmids thus digested were bonded together and used for transfecting competent cells of *E. coli*.
   The plasmidic DNA extracted from the cells of *E. coli* was then used for the tests of identification by means of PCR, restriction map and sequencing.
4. Construction of the final plasmid 2
   The plasmid 1 was digested with DraII and BclI in order to remove the immunoglobulinic promoter contained therein
   From the plasmid phMGFP, by the same digestion, the viral promoter CMV was removed
   To the plasmid 1, without promoter, by means of PCR, the promoter CMV was added so as to obtain the plasmid 2.

The following examples are intended purely as a non-limiting illustration of the invention.

Example 1

An aliquot of around 50 ml of peripheral blood originating from a patient, with the addition of a suitable aliquot of anticoagulant, is transferred into 50 ml tubes, diluted 1:1 with buffer, 20 ml of Ficoll-Paque™ are added and centrifuging is carried out for 20 minutes at 2000 rpm.

After centrifuging, the lymphocytes, contained in the interface band, are harvested and transferred into a new tube and washed 3 times in PBS (without $Ca^{++}$ and $Mg^{++}$) with recovery by centrifuging.

An aliquot of lymphocytes is diluted 1:1 in tryptan blue and counted in a haemocytometer with the microscope in order to determine the vitality thereof (at least 90%).

After the count, the lymphocytes are re-suspended at a concentration of $20 \times 10^6$ cells per ml in PBS and aliquoted into plates provided with wells with U-shaped bases. There are then added 25 μg of a plasmid, having the sequence shown in SEQ ID NO: 1, and the plate is placed in an incubator for 60-90 minutes at 37° C. and 5% of $CO_2$.

The cells are then diluted to a concentration of $1 \times 10^6$ cells per ml in suitable culture medium, placed in flasks inside an incubator and left for one night at 37° C. and 5% of $CO_2$. After having verified that the cellular vitality is above 70%, the cells are washed twice in saline solution, the number of total cells containing the dose to be inoculated is then calculated, corresponding to a number of cells variable from 10,000 to 100 million and the latter are then re-suspended in an endovenous administration bag, which is then used for inoculation into the patient.

An aliquot of the transfected lymphocytes is tested before use by means of the extraction of DNA and mRNA in a nested PCR test in such a way as to evaluate the transfection of lymphocytes that has occurred and give a quantification thereof, even approximate.

FIG. 6 shows the amplification with a PCR test of the DNA from human lymphocytes transfected with plasmidic DNA. Ladder is the reference for the determination of the dimension of the amplified fragments. The numbers refer to the number of cells amplified, and Naïve means lymphocytes not transfected with DNA (negative control). The figure demonstrates the transfection of the patient's lymphocytes which has taken place, and above all denotes its specificity, inasmuch as no fragment is amplified from lymphocytes not subjected to transfection.

Example 2

Proceeding from the assumption that the lymphocytes transfected with a DNA encoding antigenic sequences are capable of evoking an immune response after inoculation into laboratory animals and that the plasmid of the present invention, shown in SEQ ID NO: 1, encodes an epitope capable of evoking a cellular response on the part of the T CD4 lymphocytes, in order to verify the biological activity of the lymphocytes transfected by DNA, an experiment was planned for the verification of the immunogenicity of such lymphocytes in vivo, devised as described hereinafter.

- 4 C57/B16 mice were inoculated with 5,000 murine lymphocytes transfected with the plasmid as described in the protocol contained in the present invention. Inoculation was carried out endovenously in the tail vein;
- 14 days after inoculation, the mice were sacrificed and the cells of the spleen were used in a test of proliferation in the presence of the epitope encoded by the plasmid used for transfection;
- the splenocytes were cultured for 72 hours with the epitope of reference, and then tritiated timidine (a radioisotope capable of showing the cellular proliferation) was added thereto;
- after 18 hours, the cells were harvested and the radioactivity measured with a beta counter instrument. The proliferation was expressed as stimulation index (SI), which is calculated by dividing the radioactive counts in the presence of the specific epitope by the radioactive counts in the presence of an uncorrelated epitope (non-specific proliferation). Conventionally, an SI of more than 3 is considered positive.

The experiment described above showed a specific immune response induced in mice when immunized with lymphocytes transfected with the plasmidic DNA, proving a clear biological property thereof when used in a test in vivo.

Example 3

Using a plasmid as having the sequence shown in SEQ ID NO: 2, 10 C57/B16 mice were inoculated intramuscularly, in the quadriceps, with 100 μg of DNA diluted in 100 μl of saline solution (group A). The immunization protocol consisted of a total of 3 injections separated by three weeks' interval. Another group of 10 C57/B16 were immunized in the same way, using the same plasmid with the CDRs empty (without any epitope) (group B) as control of specificity of the vaccination;

- 14 days after the last inoculation, the mice were sacrificed and the cells of the spleen were used in a test of cytotoxicity in comparison with cells pulsed with epitope (NP) encoded by the plasmid used for transfection. The specific epitope is a cytotoxic sequence of the nucleoprotein of Influenza Virus A/PR8;
- the splenocytes were cultured for 5 days with the epitope of reference and then used as effectric cells in a cytotoxicity test;
- the cytotoxicity test consists in measuring the radioactivity ($^{51}$Cr) released by cells (EL-4) pulsed with epitope NP which are killed by the effectric cells from the immunized mice; the cytotoxicity is expressed as a percentage of lysis at a certain ratio of Effectrics:Target (E:T), which is calculated by dividing the amount of radioactivity released by the cells pulsed with the peptide by the amount of radioactivity released by the non-pulsed cells (specific cytotoxicity).

TABLE II

Example of cytotoxicity mediated by specific T CD8 cells in animals immunized with the plasmidic DNA #2.

| Group | % of specific lysis |
| --- | --- |
| A | 50% + 12 |
| B (control) | 3% + 2 |

The experiment described above shows the specific immune response induced in mice when immunized with plasmidic DNA, proving a clear biological property thereof when used in a test in vivo.

I claim:

1. A recombinant plasmid having the sequence set forth in SEQ ID NO: 1.

\* \* \* \* \*

SEQUENCE LISTING

```
<160> NUMBER OF SEQ ID NOS: 2

<210> SEQ ID NO 1
<211> LENGTH: 9727
<212> TYPE: DNA
<213> ORGANISM: Artificial Sequence
<220> FEATURE:
<223> OTHER INFORMATION: plasmid having immunologic action

<400> SEQUENCE: 1
aattcttcag atacaaagaa tctctaaacc ctgaggacat tctatcacaa ataagtaaaa      60
ttcagaaaat tctgaatgct cccatcacag agatgaatct gctatgaaca gctcataggt     120
gtgaagctct acaaaagcca tattattgaa aagccacatt gtgcccagac tttggaaaga     180
ctgagctcat atcctgaaat acagttatgt gtggttctat ctaattacac atttacacta     240
aggaaacatg gcagtatggg aatgaagctt gttctgtaca cattaacaga gggaaactaa     300
acaaagtatg gtgaatccct aaccaaaagt aaaaaaaaaa aaaaaaaaga aagaaaaga     360 aaaaaaaagt gaaactacaa tatgtttcaa atgctgtaac tgaaatctgg ttttttgatg     420
ccttatatct gttatcatca gtgacttcag atttagtcca actccagagc atggtatagc     480
aggaagacat gcaaataggt cttctctgtg cccatgaaaa acacctcggc cctgaccctg     540
cagctctgac agaggaggcc tgtcctggat tcgattccca gttcctcaca ttcagtgatc     600
```

```
agcactgaac acagacccct caccatgaac ttcgggctca gattgatttt ccttgtcctt    660
gttttaaaag gtaatttatt gagaatagag gacatctgtt gtatgcacag aggtacagaa    720
aaaatgttgt ttgttttttt tagtgacaat tttccaaaca gtattctttc tttgcaggtg    780
tcctgtgtga cgtgaagctc gtggagtctg ggggaggctt agtgaagctt ggagggtccc    840
tgaaactctc ctgtgcagcc tctggattca cttttcagtag gtattacatg tattacctat    900
tcttctacag aaagtcagtc atcatgtctt gggttcgcca gactccagag aagaggctgg    960
agttggtcgc agccattaat agtaatggcc atggtaatgc aaacccaaat gtagatccca   1020
atgccaaccc acatggtagc acctactatc cagacactgt gaagggccga ttcaccatct   1080
ccagagacaa tgccaaaaac accctgtacc tgcaaatgag cagtctgaag tctgaggaca   1140
cagccttgta ttactgtgca agaaaggtac aaatcctggc caagttcctg cactggctgg   1200
taccctactc tcatggtatg gactactggg gtcaaggaac ctcagtcacc gtctcctcag   1260
gtaagaatgg cctctccagg tctttatttt taacctttgt tatggagttt tctgagcatt   1320
gcagactaat cttggatatt tgtccctgag ggagccggct gagagaagtt gggaaataaa   1380
ctgtctaggg atctcagagc ctttaggaca gattatctcc acattttga aaaactaaga   1440
atctgtgtga tggtgttggt ggagtccctg gatgatggga tagggacttt ggaggctcat   1500
ttgagggaga tgctaaaaca atcctatggc tggagggata gttggggctg taattggaga   1560
ttttcagttt ttagaataaa agtattagct gcggaatata cttcaggacc acctctgtga   1620
cagcatttat acagtatccg atgcataggg acaaagagtg gagtgggggca ctttctttag   1680
atttgtgagg aatgttccac actagattgt ttaaaacttc atttgttgga aggagagctg   1740
tcttagtgat tgagtcaagg gagaaaggca tctaggctcg gtctcaaaag ggtagttgct   1800
gtctagagag gtctggtgga gcctgcaaaa gtccagcttt caaaggaaca cagaagtatg   1860
tgtatggaat attagaagat gttgctttta ctcttaagtt ggttcctagg aaaaatagtt   1920
aaatactgtg actttaaaat gtgagagggt tttcaagtac tcatttttt aaatgtccaa   1980
aattttttgtc aatcaatttg aggtcttgtt tgtgtagaac tgacattact taaagtttaa   2040
ccgaggaatg ggagtgaggc tctctcatac cctattcaga actgactttt aacaataata   2100
aattaagttt aaaatatttt taaatgaatt gagcaatgtt gagttggagt caagatggcc   2160
gatcagaacc agaacacctg cagcagctgg caggaagcag gtcatgtggc aaggctattt   2220
ggggaaggga aaataaaacc actaggtaaa cttgtagctg tggtttgaag agtggttttt   2280
gaaacactct gtccagcccc accaaaccga aagtccaggc tgagcaaaac accacctggg   2340
taatttgcat ttctaaaata agttgaggat tcagccgaaa ctggagaggt cctcttttaa   2400
cttattgagt tcaacctttt aattttagct tgagtagttc tagtttcccc aaacttaagt   2460
ttatcgactt ctaaaatgta tttagaattc attttcaaaa ttaggttatg taagaaattg   2520
aaggacttta gtgtctttaa tttctaatat atttagaaaa cttcttaaaa ttactctatt   2580
attcttccct ctgattattg gtctccattc aattcttttc caatacccga agcatttaca   2640
gtgactttgt tcatgatctt ttttagttgt ttgttttgcc ttactattaa gactttgaca   2700
ttctggtcaa aacggcttca caaatctttt tcaagaccac tttctgagta ttcatttag   2760
gagaaatact tttttttaa atgaatgcaa ttatctagac ttatttcggt tgaacatgct   2820
ggttggtggt tgagaggaca ctcagtcagt cagtggcgtg aagggcttct aagccagtcc   2880
acatgctctg tgtgaactcc ctctggcccct gctattgtt gaatgggcca aaggtctgag   2940
accaggctgc tgctgggtag gcctggactt tgggtctccc acccagacct gggaatgtat   3000
```

-continued

| | |
|---|---|
| ggttgtggct tctgccaccc atccacctgg ctgctcatgg accagccagc ctcggtggct | 3060 |
| ttgaaggaac aattccacac aaagactctg gacctctccg aaaccaggca ccgcaaatgg | 3120 |
| taagccagag gcagccacag ctgtggctgc tgctcttaaa gcttgtaaac tgtttctgct | 3180 |
| taagagggac tgagtcttca gtcattgctt taggggagaa aagagacatt tgtgtgtctt | 3240 |
| ttgagtaccg ttgtctgggt cactcaggtc gaccggtcga ccccaggcct gaccttggct | 3300 |
| ttggggcagg gaggggggcta aggtgaggca ggtggcgcca gccaggtgca cacccaatgc | 3360 |
| ccatgagccc agacactgga cgctgaacct cgcggacagt taagaaccca ggggcctctg | 3420 |
| cgccctgggc ccagctctgt cccacaccgc ggtcacatgg caccacctct cttgcagcct | 3480 |
| ccaccaaggg cccatcggtc ttccccctgg caccctcctc aagagcacc tctgggggca | 3540 |
| cagcggccct gggctgcctg gtcaaggact acttccccga accggtgacg gtgtcgtgga | 3600 |
| actcaggcgc cctgaccagc ggcgtgcaca ccttcccggc tgtcctacag tcctcaggac | 3660 |
| tctactccct cagcagcgtg gtgaccgtgc cctccagcag cttgggcacc cagacctaca | 3720 |
| tctgcaacgt gaatcacaag cccagcaaca ccaaggtgga caagaaagtt ggtgagaggc | 3780 |
| cagcacaggg agggagggtg tctgctggaa gccaggctca gacgactcct gcctggacgc | 3840 |
| atcccggcta tgcagcccca gtccagggca gcaaggcagg ccccgtctgc ctcttcaccc | 3900 |
| ggaggcctct gcccgcccca ctcatgctca gggagagggt cttctggctt tttccccagg | 3960 |
| ctctgggcag gcacaggcta ggtgccccta acccaggccc tgcacacaaa ggggcaggtg | 4020 |
| ctgggctcag acctgccaag agccatatcc gggaggaccc tgcccctgac ctaagcccac | 4080 |
| cccaaaggcc aaactctcca ctccctcagc tcggacacct tctctcctcc cagattccag | 4140 |
| taactcccaa tcttctctct gcagagccca aatcttgtga caaaactcac acatgcccac | 4200 |
| cgtgcccagg taagccagcc caggcctcgc cctccagctc aaggcgggac aggtgcccta | 4260 |
| gagtagcctg catccaggga caggccccag ccgggtgctg acacgtccac ctccatctct | 4320 |
| tcctcagcac ctgaactcct ggggggaccg tcagtcttcc tcttccccc aaaacccaag | 4380 |
| gacaccctca tgatctcccg gacccctgag gtcacatgcg tggtggtgga cgtgagccac | 4440 |
| gaagaccctg aggtcaagtt caactggtac gtggacggcg tggaggtgca taatgccaag | 4500 |
| acaaagccgc gggaggagca gtacaacagc acgtaccgtg tggtcagcgt cctcaccgtc | 4560 |
| ctgcaccagg actggctgaa tggcaaggag tacaagtgca aggtctccaa caaagccctc | 4620 |
| ccagccccca tcgagaaaac catctccaaa gccaaaggtg ggacccgtgg ggtgcgaggg | 4680 |
| ccacatggac agaggccggc tcggcccacc ctctgccctg agagtgaccg ctgtaccaac | 4740 |
| ctctgtccct acagggcagc cccgagaacc acaggtgtac accctgcccc catcccggga | 4800 |
| tgagctgacc aagaaccagg tcagcctgac ctgcctggtc aaaggcttct atcccagcga | 4860 |
| catcgccgtg gagtgggaga gcaatgggca gccggagaac aactacaaga ccacgcctcc | 4920 |
| cgtgctggac tccgacggct ccttcttcct ctacagcaag ctcaccgtgg acaagagcag | 4980 |
| gtggcagcag gggaacgtct tctcatgctc cgtgatgcat gaggctctgc acaaccacta | 5040 |
| cacgcagaag agcctctccc tgtctccggg taaatgagtg cgacggccgg caagcccccg | 5100 |
| ctccccgggc tctcgcggtc gcacgaggat gcttggcacg tacccctgt acatacttcc | 5160 |
| cgggcgccca gcatggaaat aaagcaccca gcgctgccct gggcccctgc gagactgtga | 5220 |
| tggttctttc cacgggtcag ccgagtctg aggcctgagt ggcatgaggg aggcagagcg | 5280 |
| ggtcccactg tccccacact ggcccaggct gtgcaggtgt gcctgggccg ctagggtgg | 5340 |
| ggctcagcca ggggctgccc tcggcagggt gggggatttg ccagcgtggc cctccctcca | 5400 |

```
gcagcacctg ccctgggctg ggccacggga agccctagga gccctgggg acagacacac   5460
agccctgcc  tctgtaggag actgtcctgt tctgtgagcg ccctgtcctc cgacctccat   5520
gcccactcgg gggcatgcct agtccatgtg cgtagggaca ggccctccct cacccatcta   5580
cccccacggc actaacccct ggctgcctg  cccagcctcg cacccgcatg gggacacaac   5640
cgactccggg gacatgcact ctcgggccct gtggagggac tggtgcagat gcccacacac   5700
acactcagcc cagacccgtt caacaaaccc cgcactgagg ttggccggga tccagacatg   5760
ataagataca ttgatgagtt tggacaaacc acaactagaa tgcagtgaaa aaatgctttt   5820
atttgtgaaa tttgtgatgc tattgcttta tttgtaacca ttataagctg caataaacaa   5880
gttaacaaca acaattgcat tcattttatg tttcaggttc agggggaggt gtgggaggtt   5940
ttttaaagca agtaaaacct ctacaaatgt ggtatggctg attatgatct ctagtcaagg   6000
cactatacat caaatattcc ttattaaccc ctttacaaat taaaagcta  aaggtacaca   6060
atttttgagc atagttatta atagcagaca ctctatgcct gtgtggagta agaaaaaaca   6120
gtatgttatg attataactg ttatgcctac ttataaaggt tacagaatat ttttccataa   6180
ttttcttgta tagcagtgca gctttttcct tgtggtgta  aatagcaaag caagcaagag   6240
ttctattact aaacacagca tgactcaaaa aacttagcaa ttctgaagga aagtccttgg   6300
ggtcttctac ctttctcttc ttttttggag gagtagaatg ttgagagtca gcagtagcct   6360
catcatcact agatggcatt tcttctgagc aaaacaggtt ttcctcatta aaggcattcc   6420
accactgctc ccattcatca gttccatagg ttggaatcta aaatacacaa acaattagaa   6480
tcagtagttt aacacattat acacttaaaa attttatatt taccttagag ctttaaatct   6540
ctgtaggtag tttgtccaat tatgtcacac cacagaagta aggttccttc acaaagatcc   6600
ggaccaaagc ggccatcgtg cctccccact cctgcagttc gggggcatgg atgcgcggat   6660
agccgctgct ggtttcctgg atgccgacgg atttgcactg ccggtagaac tccgcgaggt   6720
cgtccagcct caggcagcag ctgaaccaac tcgcgagggg atcgagcccg ggtgggcga   6780
agaactccag catgagatcc ccgcgctgga ggatcatcca gccggcgtcc cggaaaacga   6840
ttccgaagcc caacctttca tagaaggcgg cggtggaatc gaaatctcgt gatggcaggt   6900
tgggcgtcgc ttggtcggtc atttcgaacc ccagagtccc gctcagaaga actcgtcaag   6960
aaggcgatag aaggcgatgc gctgcgaatc gggagcggcg ataccgtaaa gcacgaggaa   7020
gcggtcagcc cattcgccgc caagctcttc agcaatatca cgggtagcca acgctatgtc   7080
ctgatagcgg tccgccacac ccagccgccc acagtcgatg aatccagaaa agcggccatt   7140
ttccaccatg atattcggca agcaggcatc gccatgggtc acgacgagat cctcgccgtc   7200
gggcatgcgc gccttgagcc tggcgaacag ttcggctggc gcgagcccct gatgctcttc   7260
gtccagatca tcctgatcga caagaccggc ttccatccga gtacgtgctc gctcgatgcg   7320
atgtttcgct tggtggtcga atgggcaggt agccggatca agcgtatgca gccgccgcat   7380
tgcatcagcc atgatggata cttttctcgg caggagcaagg tgagatgaca ggagatcctg   7440
ccccggcact tcgcccaata gcagccagtc ccttcccgct tcagtgacaa cgtcgagcac   7500
agctgcgcaa ggaacgcccg tcgtggccag ccacgatagc cgcgctgcct cgtcctgcag   7560
ttcattcagg gcaccggaca ggtcggtctt gacaaaaaga accgggcgcc cctgcgctga   7620
cagccggaac acggcggcat cagagcagcc gattgtctgt tgtgcccagt catagccgaa   7680
tagcctctcc acccaagcgg ccggagaacc tgcgtgcaat ccatcttgtt caatcatgcg   7740
aaacgatcct catcctgtct cttgatcaga tcttgatccc ctgcgccatc agatccttgg   7800
```

```
cggcaagaaa gccatccagt ttactttgca gggcttccca accttaccag agggcgcccc    7860
agctggcaat tccggttcgc ttgctgtcca taaaaccgcc cagtctagct atcgccatgt    7920
aagcccactg caagctacct gctttctctt tgcgcttgcg ttttcccttg tccagatagc    7980
ccagtagctg acattcatcc ggggtcagca ccgtttctgc ggactggctt tctacgtgtt    8040
ccgcttcctt tagcagccct tgcgccctga gtgcttgcgg cagcgtgatc ccggagacgg    8100
tcacagcttg tctgtaagcg gatgccggga gcagacaagc ccgtcaggdc gcgtcagcgg    8160
gtgttggcgg gtgtcggggc gcagccatga cccagtcacg tagcgatagc ggagtgtata    8220
ctggcttaac tatgcggcat cagagcagat tgtactgaga gtgcaccata tgcggtgtga    8280
aataccgcac agatgcgtaa ggagaaaata ccgcatcagg cgctcttccg cttcctcgct    8340
cactgactcg ctgcgctcgg tcgttcggct gcggcgagcg gtatcagctc actcaaaggc    8400
ggtaatacgg ttatccacag aatcagggga taacgcagga agaacatgt gagcaaaagg    8460 ccagcaaaag gccaggaacc gtaaaaaggc cgcgttgctg gcgttttccc ataggctccg    8520
cccccctgac gagcatcaca aaaatcgacg ctcaagtcag aggtggcgaa acccgacagg    8580
actataaaga taccaggcgt ttccccctgg aagctccctc gtgcgctctc ctgttccgac    8640
cctgccgctt accggatacc tgtccgcctt tctcccttcg ggaagcgtgg cgctttctca    8700
tagctcacgc tgtaggtatc tcagttcggt gtaggtcgtt cgctccaagc tgggctgtgt    8760
gcacgaaccc cccgttcagc ccgaccgctg cgccttatcc ggtaactatc gtcttgagtc    8820
caacccggta agacacgact tatcgccact ggcagcagcc actggtaaca ggattagcag    8880
agcgaggtat gtaggcggtg ctacagagtt cttgaagtgg tggcctaact acggctacac    8940
tagaaggaca gtatttggta tctgcgctct gctgaagcca gttaccttcg gaaaaagagt    9000
tggtagctct tgatccggca aacaaaccac cgctggtagc ggtggttttt ttgtttgcaa    9060
gcagcagatt acgcgcagaa aaaaaggatc tcaagaagat cctttgatct tttctacggg    9120
gtctgacgct cagtggaacg aaaactcacg ttaagggatt ttggtcatga gattatcaaa    9180
aaggatcttc acctagatcc ttttaaatta aaaatgaagt tttaaatcaa tctaaagtat    9240
atatgagtaa acttggtctg acagttacca atgcttaatc agtgaggcac ctatctcagc    9300
gatctgtcta tttcgttcat ccatagttgc ctgactcccg ttcttcgggg cgaaaactct    9360
caaggatctt accgctgttg agatccagtt cgatgtaacc cactcgtgca cccaactgat    9420
cttcagcatc ttttactttc accagcgttt ctgggtgagc aaaaacagga aggcaaaatg    9480
ccgcaaaaaa gggaataagg gcgacacgga aatgttgaat actcatactc ttcctttttc    9540
aatattattg aagcatttat cagggttatt gtctcatgag cggatacata tttgaatgta    9600
tttagaaaaa taaacaaata ggggttccgc gcacatttcc ccgaaaagtg ccacctgacg    9660
tctaagaaac cattattatc atgacattaa cctataaaaa taggcgtatc acgaggccct    9720
ttcgtcg                                                              9727

<210> SEQ ID NO 2
<211> LENGTH: 10004
<212> TYPE: DNA
<213> ORGANISM: Artificial Sequence
<220> FEATURE:
<223> OTHER INFORMATION: plasmid having immunologic action

<400> SEQUENCE: 2
aattcttcag atacaaagaa tctctaaacc ctgaggacat tctatcacaa ataagtaaaa      60
ttcagaaaat tctgaatgct cccatcacag agatgaatct gctatgaaca gctcataggt     120
```

```
gtgaagctct acaaaagcca tattattgaa aagccacatt gtgtcaatat tggccattag    180
ccatattatt cattggttat atagcataaa tcaatattgg ctattggcca ttgcatacgt    240
tgtatctata tcataaatatg tacatttata ttggctcatg tccaatatga ccgccatgtt    300
ggcattgatt attgactagt tattaatagt aatcaattac ggggtcatta gttcatagcc    360
catatatgga gttccgcgtt acataactta cggtaaatgg cccgcctggc tgaccgccca    420 acgaccccg cccattgacg tcaataatga cgtatgttcc catagtaacg ccaatgggga    480
ctttccattg acgtcaatgg gtggagtatt tacggtaaac tgcccacttg gcagtacatc    540
aagtgtatca tatgccaagt ccgcccccta ttgacgtcaa tgacggtaaa tggcccgcct    600
ggcattatgc ccagtacatg accttacggg actttcctac ttggcagtac atctacgtat    660
tagtcatcgc tattaccatg gtgatgcggt tttggcagta caccaatggg cgtggatagc    720
ggtttgactc acggggattt ccaagtctcc accccattga cgtcaatggg agtttgtttt    780
ggcaccaaaa tcaacgggac tttccaaaat gtcgtaataa ccccgccccg ttgacgcaaa    840
tgggcggtag cgtgtacgg tgggaggtct atataagcag agctcgttta gtgaaccgtc    900
agatctgatc agcactgaac acagaccct caccatgaac ttcgggctca gattgatttt    960
ccttgtcctt gttttaaaag gtaatttatt gagaatagag acatctgtt gtatgcacag   1020 aggtacagaa aaaatgttgt tgtttttttt tagtgacaat tttccaaaca gtattctttc   1080
tttgcaggtg tcctgtgtga cgtgaagctc gtggagtctg ggggaggctt agtgaagctt   1140
ggagggtccc tgaaactctc ctgtgcagcc tctggattca ctttcagtag gtattacatg   1200
tcttgggttc gccagactcc agagaagagg ctggagttgg tcgcagccat taatagtaat   1260
ggccatggta atgcaaaccc aaatgtagat cccaatgcca acccacatgg tagcacctac   1320
tatccagaca ctgtgaaggg ccgattcacc atctccagag acaatgccaa aaacaccctg   1380
tacctgcaaa tgagcagtct gaagtctgag gacacagcct tgtattactg tgcaagaaag   1440
gtacccgctt ccaatgaaaa tatggagact atggaatcaa gtacacttgt accctactct   1500
catggtatgg actactgggg tcaaggaacc tcagtcaccg tctcctcagg taagaatggc   1560
ctctccaggt ctttatttt aacctttgtt atggagtttt ctgagcattg cagactaatc   1620
ttggatattt gtccctgagg gagccggctg agagaagttg ggaaataaac tgtctaggga   1680
tctcagagcc tttaggacag attatctcca cattttgaa aaactaagaa tctgtgtgat   1740
ggtgttggtg gagtccctgg atgatgggat agggactttg gaggctcatt tgagggagat   1800
gctaaaacaa tccatggct ggagggatag ttggggctgt aattgagat tttcagttt    1860 tagaataaaa gtattagctg cggaatatac ttcaggacca cctctgtgac agcatttata   1920
cagtatccga tgcataggga caaagagtgg agtgggcac tttctttaga tttgtgagga   1980
atgttccaca ctagattgtt taaaacttca tttgttggaa ggagagctgt cttagtgatt   2040
gagtcaaggg agaaaggcat ctaggctcgg tctcaaaagg gtagttgctg tctagagagg   2100
tctggtggag cctgcaaaag tccagctttc aaaggaacac agaagtatgt gtatggaata   2160
ttagaagatg ttgcttttac tcttaagttg gttcctagga aaaatagtta atactgtga    2220 ctttaaaatg tgagagggtt ttcaagtact catttttta aatgtccaaa attttgtca    2280 atcaatttga ggtcttgttt gtgtagaact gacattactt aaagtttaac cgaggaatgg   2340
gagtgaggct ctctcatacc ctattcagaa ctgacttta acaataataa attaagttta   2400 aaatatttt aaatgaattg agcaatgttg agttggagtc aagatggccg atcagaacca   2460
gaacacctgc agcagctggc aggaagcagg tcatgtggca aggctatttg ggaagggaa    2520
```

```
aataaaacca ctaggtaaac ttgtagctgt ggtttgaaga agtggttttg aaacactctg    2580
tccagcccca ccaaaccgaa agtccaggct gagcaaaaca ccacctgggt aatttgcatt    2640
tctaaaataa gttgaggatt cagccgaaac tggagaggtc ctcttttaac ttattgagtt    2700 caaccttttta attttagctt gagtagttct agtttcccca aacttaagtt tatcgacttc    2760
taaaatgtat ttagaattca ttttcaaaat taggttatgt aagaaattga aggactttag    2820
tgtctttaat ttctaatata tttagaaaac ttcttaaaat tactctatta ttcttccctc    2880
tgattattgg tctccattca attcttttcc aatacccgaa gcatttacag tgactttgtt    2940
catgatcttt tttagttgtt tgttttgcct tactattaag actttgacat tctggtcaaa    3000
acggcttcac aaatctttt caagaccact ttctgagtat tcattttagg agaaatactt    3060 ttttttaaa tgaatgcaat tatctagact tatttcggtt gaacatgctg gttggtggtt    3120
gagaggacac tcagtcagtc agtggcgtga agggcttcta agccagtcca catgctctgt    3180
gtgaactccc tctggccctg cttattgttg aatgggccaa aggtctgaga ccaggctgct    3240
gctgggtagg cctggacttt gggtctccca cccagacctg gaatgtatg gttgtggctt    3300 ctgccaccca tccacctggc tgctcatgga ccagccagcc tcggtggctt tgaaggaaca    3360
attccacaca aagactctgg acctctccga aaccaggcac cgcaaatggt aagccagagg    3420
cagccacagc tgtggctgct gctcttaaag cttgtaaact gtttctgctt aagagggact    3480
gagtcttcag tcattgcttt aggggggagaa agagacattt gtgtgtcttt tgagtaccgt    3540
tgtctgggtc actcaggtcg accggtcgac cccaggcctg accttggctt tggggcaggg    3600 aggggggctaa ggtgaggcag gtggcgccag ccaggtgcac acccaatgcc catgagccca    3660
gacactggac gctgaacctc gcggacagtt aagaacccag gggcctctgc gccctgggcc    3720
cagctctgtc ccacaccgcg gtcacatggc accacctctc ttgcagcctc caccaagggc    3780
ccatcggtct tcccccctggc accctcctcc aagagcacct ctgggggcac agcggcctg    3840 ggctgcctgg tcaaggacta cttccccgaa ccggtgacgg tgtcgtggaa ctcaggcgcc    3900
ctgaccagcg gcgtgcacac cttcccggct gtcctacagt cctcaggact ctactccctc    3960
agcagcgtgg tgaccgtgcc ctccagcagc ttgggcaccc agacctacat ctgcaacgtg    4020
aatcacaagc ccagcaacac caaggtggac aagaaagttg gtgagaggcc agcacaggga    4080
gggagggtgt ctgctggaag ccaggctcag acgactcctg cctggacgca tcccggctat    4140
gcagccccag tccagggcag caaggcaggc cccgtctgcc tcttcacccg gaggcctctg    4200
cccgccccac tcatgctcag ggagagggtc ttctggcttt ttccccaggc tctgggcagg    4260
cacaggctag gtgcccctaa cccaggccct gcacacaaag gggcaggtgc tgggctcaga    4320
cctgccaaga gccatatccg ggaggaccct gcccctgacc taagcccacc ccaaaggcca    4380
aactctccac tccctcagct cggacacctt ctctcctccc agattccagt aactcccaat    4440
cttctctctg cagagcccaa atcttgtgac aaaactcaca catgcccacc gtgcccaggt    4500
aagccagccc aggcctcgcc ctccagctca aggcgggaca ggtgccctag agtagcctgc    4560
atccagggac aggccccagc cgggtgctga cacgtccacc tccatctctt cctcagcacc    4620
tgaactcctg gggggaccgt cagtcttcct cttccccca aaacccaagg acaccctcat    4680
gatctcccgg acccctgagg tcacatgcgt ggtggtggac gtgagccacg aagaccctga    4740
ggtcaagttc aactggtacg tggacggcgt ggaggtgcat aatgccaaga caaagccgcg    4800
ggaggagcag tacaacagca cgtaccgtgt ggtcagcgtc ctcaccgtcc tgcaccagga    4860
ctggctgaat ggcaaggagt acaagtgcaa ggtctccaac aaagccctcc cagcccccat    4920
```

| | |
|---|---|
| cgagaaaacc atctccaaag ccaaaggtgg gacccgtggg gtgcgagggc cacatggaca | 4980 |
| gaggccggct cggcccaccc tctgccctga gagtgaccgc tgtaccaacc tctgtcccta | 5040 |
| cagggcagcc ccgagaacca caggtgtaca ccctgccccc atcccgggat gagctgacca | 5100 |
| agaaccaggt cagcctgacc tgcctggtca aaggcttcta tcccagcgac atcgccgtgg | 5160 |
| agtgggagag caatgggcag ccggagaaca actacaagac cacgcctccc gtgctggact | 5220 |
| ccgacggctc cttcttcctc tacagcaagc tcaccgtgga caagagcagg tggcagcagg | 5280 |
| ggaacgtctt ctcatgctcc gtgatgcatg aggctctgca caaccactac acgcagaaga | 5340 |
| gcctctccct gtctccgggt aaatgagtgc gacggccggc aagccccgc tccccgggct | 5400 |
| ctcgcggtcg cacgaggatg cttggcacgt accccctgta catacttccc gggcgcccag | 5460 |
| catgaaaata aagcacccag cgctgccctg ggccctgcg agactgtgat ggttctttcc | 5520 |
| acgggtcagg ccgagtctga ggcctgagtg gcatgaggga ggcagagcgg gtcccactgt | 5580 |
| ccccacactg gccaggctg tgcaggtgtg cctgggccgc ctagggtggg gctcagccag | 5640 |
| gggctgccct cggcagggtg ggggattgc cagcgtggcc ctccctccag cagcacctgc | 5700 |
| cctgggctgg gccacgggaa gccctaggag cccctgggga cagacacaca gccctgcct | 5760 |
| ctgtaggaga ctgtcctgtt ctgtgagcgc cctgtcctcc gacctccatg cccactcggg | 5820 |
| ggcatgccta gtccatgtgc gtagggacag gccctccctc acccatctac ccccacggca | 5880 |
| ctaacccctg gctgccctgc ccagcctcgc acccgcatgg ggacacaacc gactccgggg | 5940 |
| acatgcactc tcgggccctg tggagggact ggtgcagatg cccacacaca cactcagccc | 6000 |
| agacccgttc aacaaacccc gcactgaggt tggccgggat ccagacatga taagatacat | 6060 |
| tgatgagttt ggacaaacca caactagaat gcagtgaaaa aaatgcttta tttgtgaaat | 6120 |
| ttgtgatgct attgctttat ttgtaaccat tataagctgc aataaacaag ttaacaacaa | 6180 |
| caattgcatt cattttatgt ttcaggttca gggggaggtg tgggaggttt tttaaagcaa | 6240 |
| gtaaaacctc tacaaatgtg gtatggctga ttatgatctc tagtcaaggc actatacatc | 6300 |
| aaatattcct tattaacccc tttacaaatt aaaaagctaa aggtacacaa tttttgagca | 6360 |
| tagttattaa tagcagacac tctatgcctg tgtggagtaa gaaaaaacag tatgttatga | 6420 |
| ttataactgt tatgcctact tataaaggtt acagaatatt tttccataat tttcttgtat | 6480 |
| agcagtgcag cttttccctt tgtggtgtaa atagcaaagc aagcaagagt tctattacta | 6540 |
| aacacagcat gactcaaaaa acttagcaat tctgaaggaa agtccttggg gtcttctacc | 6600 |
| tttctcttct ttttggagg agtagaatgt tgagagtcag cagtagcctc atcatcacta | 6660 |
| gatggcattt cttctgagca aaacaggttt tcctcattaa aggcattcca ccactgctcc | 6720 |
| cattcatcag ttccataggt tggaatctaa aatacacaaa caattagaat cagtagttta | 6780 |
| acacattata cacttaaaaa ttttatattt accttagagc tttaaatctc tgtaggtagt | 6840 |
| ttgtccaatt atgtcacacc acagaagtaa ggttccttca caaagatccg gaccaaagcg | 6900 |
| gccatcgtgc ctccccactc ctgcagttcg ggggcatgga tgcgcggata gccgctgctg | 6960 |
| gtttcctgga tgccgacgga tttgcactgc cggtagaact ccgcgaggtc gtccagcctc | 7020 |
| aggcagcagc tgaaccaact cgcgagggga tcgagcccgg ggtgggcgaa gaactccagc | 7080 |
| atgagatccc cgcgctggag gatcatccag ccggcgtccc ggaaaacgat tccgaagccc | 7140 |
| aacctttcat agaaggcggc ggtggaatcg aaatctcgtg atggcaggtt gggcgtcgct | 7200 |
| tggtcggtca tttcgaaccc cagagtcccg ctcagaagaa ctcgtcaaga aggcgataga | 7260 |
| aggcgatgcg ctgcgaatcg ggagcggcga taccgtaaag cacgaggaag cggtcagccc | 7320 |

```
attcgccgcc aagctcttca gcaatatcac gggtagccaa cgctatgtcc tgatagcggt    7380
ccgccacacc cagccggcca cagtcgatga atccagaaaa gcggccattt tccaccatga    7440
tattcggcaa gcaggcatcg ccatgggtca cgacgagatc ctcgccgtcg gcatgcgcg    7500
ccttgagcct ggcgaacagt tcggctggcg cgagcccctg atgctcttcg tccagatcat    7560
cctgatcgac aagaccggct tccatccgag tacgtgctcg ctcgatgcga tgtttcgctt    7620
ggtggtcgaa tgggcaggta gccggatcaa gcgtatgcag ccgccgcatt gcatcagcca    7680
tgatggatac tttctcggca ggagcaaggt gagatgacag agatcctgc cccggcactt    7740
cgcccaatag cagccagtcc cttcccgctt cagtgacaac gtcgagcaca gctgcgcaag    7800
gaacgcccgt cgtggccagc cacgatagcc gcgctgcctc gtcctgcagt tcattcaggg    7860
caccggacag gtcggtcttg acaaaaagaa ccgggcgccc ctgcgctgac agccggaaca    7920
cggcggcatc agagcagccg attgtctgtt gtgcccagtc atagccgaat agcctctcca    7980
cccaagcggc cggagaacct gcgtgcaatc catcttgttc aatcatgcga aacgatcctc    8040
atcctgtctc ttgatcagat cttgatcccc tgcgccatca gatccttggc ggcaagaaag    8100
ccatccagtt tactttgcag ggcttcccaa ccttaccaga gggcgcccca gctggcaatt    8160
ccggttcgct tgctgtccat aaaaccgccc agtctagcta tcgccatgta agcccactgc    8220
aagctacctg cttctctttt gcgcttgcgt tttcccttgt ccagatagcc cagtagctga    8280
cattcatccg gggtcagcac cgtttctgcg gactggcttt ctacgtgttc cgcttccttt    8340
agcagccctt gcgccctgag tgcttgcggc agcgtgatcc cggagacggt cacagcttgt    8400
ctgtaagcgg atgccgggag cagacaagcc cgtcagggcg cgtcagcggg tgttggcggg    8460
tgtcggggcg cagccatgac ccagtcacgt agcgatagcg gagtgtatac tggcttaact    8520
atgcggcatc agagcagatt gtactgagag tgcaccatat gcggtgtgaa ataccgcaca    8580
gatgcgtaag gagaaaatac cgcatcaggc gctcttccgc ttcctcgctc actgactcgc    8640
tgcgctcggt cgttcggctg cggcgagcgg tatcagctca ctcaaaggcg gtaatacggt    8700
tatccacaga atcaggggat aacgcaggaa agaacatgtg agcaaaaggc cagcaaaagg    8760
ccaggaaccg taaaaaggcc gcgttgctgg cgtttttcca taggctccgc cccctgacg    8820
agcatcacaa aaatcgacgc tcaagtcaga ggtggcgaaa cccgacagga ctataaagat    8880
accaggcgtt ccccctgga agctccctcg tgcgctctcc tgttccgacc ctgccgctta    8940
ccggatacct gtccgccttt ctcccttcgg gaagcgtggc gctttctcat agctcacgct    9000
gtaggtatct cagttcggtg taggtcgttc gctccaagct gggctgtgtg cacgaacccc    9060
ccgttcagcc cgaccgctgc gccttatccg gtaactatcg tcttgagtcc aacccggtaa    9120
gacacgactt atcgccactg gcagcagcca ctggtaacag gattagcaga gcgaggtatg    9180
taggcggtgc tacagagttc ttgaagtggt ggcctaacta cggctacact agaaggacag    9240
tatttggtat ctgcgctctg ctgaagccag ttaccttcgg aaaaagagtt ggtagctctt    9300
gatccggcaa acaaaccacc gctggtagcg gtggtttttt tgtttgcaag cagcagatta    9360
cgcgcagaaa aaaaggatct caagaagatc ctttgatctt ttctacgggg tctgacgctc    9420
agtggaacga aaactcacgt taagggattt tggtcatgag attatcaaaa aggatcttca    9480
cctagatcct tttaaattaa aaatgaagtt ttaaatcaat ctaaagtata tatgagtaaa    9540
cttggtctga cagttaccaa tgcttaatca gtgaggcacc tatctcagcg atctgtctat    9600
ttcgttcatc catagttgcc tgactcccgt tcttcggggc gaaaactctc aaggatctta    9660
ccgctgttga gatccagttc gatgtaaccc actcgtgcac ccaactgatc ttcagcatct    9720
```

-continued

| | | | | |
|---|---|---|---|---|
| tttactttca | ccagcgtttc | tgggtgagca | aaaacaggaa | ggcaaaatgc cgcaaaaaag 9780 |
| ggaataaggg | cgacacggaa | atgttgaata | ctcattcaat | attattgaag catttatcag 9840 |
| ggttattgtc | tcatgagcgg | atacatattt | gaatgtattt | agaaaaataa acaaataggg 9900 |
| gttccgcgca | catttccccg | aaaagtgcca | cctgacgtct | aagaaaccat tattatcatg 9960 |
| acattaacct | ataaaaatag | gcgtatcacg | aggccctttc | gtcg 10004 |